US009678063B2

(12) United States Patent
Lobocka et al.

(10) Patent No.: US 9,678,063 B2
(45) Date of Patent: Jun. 13, 2017

(54) METHOD OF EVALUATING THE THERAPEUTIC EFFICACY OF BACTERIOPHAGES

(71) Applicants: Instytut Biochemii I biofizyki Polskiej Akademii Nauk, Warsaw (PL); Instytut Immunologii I Terapii Doswiadczalnej Polskiej Akademii Nauk, Wroclaw (PL); Narodowy Instytut Lekow, Warsaw (PL); Szkola Glowna Gospodarstwa Wiejskiego W Warszawie, Warsaw (PL); Wojskowy Instytut Higieny I Epiemiologii, Warsaw (PL)

(72) Inventors: Malgorzata Lobocka, Warsaw (PL); Aleksandra Glowacka, Zyrardow (PL); Kamil Dabrowski, Sulejowek (PL); Monika S. Hejnowicz, Horyniec-Zdroj (PL); Agnieszka Gozdek, Warsaw (PL); Beata Weber-Dabrowska, Wroclaw (PL); Andrzej Gorski, Wroclaw (PL); Joanna Empel, Warsaw (PL); Waleria Hryniewicz, Warsaw (PL); Magdalena Kwiatek, Pulawy (PL); Sylwia Parasion, Lublin (PL); Romuald Gryko, Pulawy (PL)

(73) Assignees: Instytut Biochemii i Biofizyki Polskiej Akademii Nauk, Warsaw (PL); Instytut Immunolii i Terapii Doswiadczalnej Polskiej Akademii Nauk, Warsaw (PL); Narodowy Instytut Lekow, Warsaw (PL); Szkola Gowna Gospodarstwa Wiejskiego w Warzawie, Warsaw (PL); Wojskowy Instytut Higieny i Epidemiologii, Warsaw (PL)

( * ) Notice: Subject to any disclaimer, the term of this patent is extended or adjusted under 35 U.S.C. 154(b) by 0 days.

(21) Appl. No.: 14/414,486

(22) PCT Filed: Jul. 13, 2013

(86) PCT No.: PCT/EP2013/064870
§ 371 (c)(1),
(2) Date: Jan. 13, 2015

(87) PCT Pub. No.: WO2014/012872
PCT Pub. Date: Jan. 23, 2014

(65) Prior Publication Data
US 2015/0192569 A1 Jul. 9, 2015

(30) Foreign Application Priority Data

Jul. 14, 2012 (PL) .................................... 399961

(51) Int. Cl.
*A61K 49/00* (2006.01)
*A61K 39/02* (2006.01)
*A01N 63/00* (2006.01)
*G01N 33/50* (2006.01)
*A61K 35/76* (2015.01)

(52) U.S. Cl.
CPC .......... *G01N 33/5085* (2013.01); *A61K 35/76* (2013.01); *G01N 2333/4353* (2013.01)

(58) Field of Classification Search
CPC ........................................................ A61K 35/76
USPC ...................................... 424/9.1, 9.2, 234.1
See application file for complete search history.

(56) References Cited

PUBLICATIONS

Moy, T.I., et al., PNAS, vol. 103, No. 27, pp. 10414-10419, Jul. 2006.*
Santander, J., et al., Electronic Journal of Biotechnology, vol. 7, No. 2, pp. 208-211, 2004.*
Santander et al., "Bacteriophage prophylaxis against *Salmonella enteritidis* and *Salmonella pullorum* using Caenorhabditis elegans as an assay system," Electronic Journal of Biotechnology (Aug. 15, 2004); 7(2):208-211.
Moy et al., "Identification of novel antimirobials using a live-animal infection model," PNAS (Jul. 5, 2006); 103(27):10414-10419.
Matsuzaki et al., "Bacteriophage therapy: a revitalized therapy against bacterial infectious diseases," J. Infect Chemother (2005); 11:211-219.
Sulakvelidze et al., "Bacteriophage Therapy," Antimicrobial Agents and Chemotherapy (Mar. 2001); 45(3):649-659.
Spizek et al., "Do we need new antibiotics? The search for new targets and new compounds," J. Ind. Microbiol Biotechnol (2010); 37:1241-1248.
Govind, Pandey "Model Organisms Used in Molecular Biology or Medical Research," IRJP (2011); 2(11):62-65.
Levin, Bruce R. et al., Population and evolutionary dynamics of phage therapy; Nature Reviews (2003) Macmillan Magazines Ltd.; vol. 2, Feb. 2004, pp. 166-173.
Nordstrom, Kristina et al., Prevention of Bacteriophage Adsorption to *Staphylococcus aureus* by Immunoglobulin G; Journal of Virology, Aug. 1974. vol. 14, No. 2, p. 203-206.
Payne, Robert J.H. et al., Understanding Bacteriophage Therapy as a Density-dependent Kinetic Process; J. Theor. Biol. (2001) 208, 37-48.
Smith, H. Williams et al., Factors Influencing the Survival and Multiplication of Bacteriophages in Calves and in Their Environment; Journal of General Microbiology (1987), 133, 1127-1135.
Zhao, Piceng et al., Antiviral, anti-parasitic, and cytotoxic effects of 5,6-dihydroxyindole (DHI), a reactive compound generated by phenoloxidase during insect immune reponse; Insect and Biochemistry and Molecular Biology 41 (2011) 645-652.

* cited by examiner

*Primary Examiner* — Rodney P Swartz
(74) *Attorney, Agent, or Firm* — Fox Rothschild LLP

(57) ABSTRACT

The subject of the present invention is a novel use of a nematode in the evaluation of the therapeutic efficacy of bacteriophage preparations used in, or capable of being used in the treatment of infections caused by pathogenic bacteria in humans or animals.

4 Claims, 15 Drawing Sheets

Fig. 7 (continuation) :
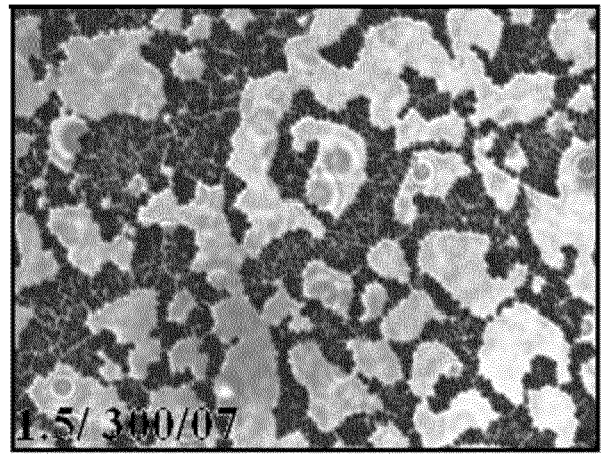

A  B  C

D

METHOD OF EVALUATING THE THERAPEUTIC EFFICACY OF BACTERIOPHAGES

This application is a U.S. National Phase of International Application No. PCT/EP2013/064870, filed Jul. 13, 2013, which claims priority of Poland Application No. 399961, filed Jul. 14, 2012. The contents of both applications are incorporated herein by reference in their entirety.

The subject of the present invention is a new method of testing the therapeutic utility of bacteriophage preparations, useful for the large scale, rapid preselection of bacteriophages with a high therapeutic potential.

Due to the serious crisis in antibiotic therapy caused by an increasing number of bacterial strains resistant to available antibiotics, the amount of effort into seeking or designing novel antibacterial drugs and their evaluation and marketing are of key significance for saving human and animal lives. Naturally occurring bacteriophages, bacterial viruses, are a group of potential new-generation antibacterial drugs. They infect specific cells of their bacterial hosts and are harmless to eukaryotic cells. Experiments using phages in the treatment of infections in animals clearly show the efficacy of appropriately selected bacteriophages in the treatment of bacterial infections.

The key factor in future research on therapeutic efficacy is the ability to select bacteriophages with high in vivo efficacy from the countless number available in the environment or in bacteriophage collections, and the ability to identify those genes from the numerous phage genes of unknown function, whose modification or natural recombinant exchange between phages, would make it possible to produce therapeutic phages with better properties (i.e. broadened or narrowed specificity in relation to bacterial strains in an infection model, increased stability in the treated animal or human organism).

To date, selection methods for bacteriophages with potential therapeutic utility are almost exclusively based on testing both bacteriophages infectiousness against defined bacteria, as well as their rate of proliferation and lytic efficacy in bacterial cultures in laboratory media. For financial and ethical considerations, in infrequent animal infection tests on the efficacy of phage therapy, subject to strict regulations, only a few phages are selected that have been tested in vitro, without the possibility of initially preselecting those best suited for in vivo use.

Numerous reports on bacterial pathogenesis indicate significant differences in the physiology, gene expression, metabolism, envelope and biofilm formation as well as a series of other properties of bacterial pathogens residing in the organism attacked or infected by them, in relation to bacteria residing outside of an organism, including lab-cultured ones. Moreover, the conditions inside an organism invaded by bacteria are subject to so many factors, that it is impossible to recreate them artificially. All of this makes for the fact that bacteriophages effective in the eradication of bacteria in laboratory cultures can become ineffective after their administration into a eukaryotic organism infected by the same bacteria. There are numerous examples of such differences in literature.

The goal of the present invention is to deliver a rapid, inexpensive and ethically unconstrained method capable of large-scale application facilitating the testing and comparison of the therapeutic efficacy of bacteriophages in the elimination of an infection from a eukaryotic organism infected by bacteria specific for said bacteriophage in vivo.

In the selection of a model system for designing this method, it was assumed that it must be based on the evaluation of the therapeutic efficacy of bacteriophages in a simple, multicellular eukaryotic organism possessing separable organs, which is infected by the bacterial pathogens of animals and humans, which has a completely known genome and is easily cultured, wherein its innate immune system is similar to the human one, and the effectiveness of therapy in the form of the eradication of pathogenic bacteria can be monitored in real time during and after therapy. The nematode *Caenorhabditis elegans* is such an organism.

A series of bacteria pathogenic to humans and homeothermic animals, such as bacteria of the genera *Staphylococcus, Enterococcus, Pseudomonas, Salmonella, Shigella, Vibrio, Escherichia, Cronobacter* and many others exhibit pathogenicity to the nematode. Infection by these bacteria are lethal to the nematode. For this reason *C. elegans* is used as a model for pathogenesis studies. These studies have resulted in the identification of a series of bacterial genes encoding virulence factors. To compare the pathogenicity of various bacterial strains against the nematode one uses a simple survivability assay, which determines the time at which the death of half of the nematodes infected by a given pathogen occurs (so-called LT50).

Most of the bacterial strains pathogenic to humans, including *Staphylococcus aureus*, cause infections and destruction of the nematode gut. Bacteria from the damaged gut enter the remaining portions of the organism, which leads to a general infection and mortality.

Nematodes naturally feed on bacteria, which constitutes an easy pathway for administering them bacterial pathogens into the gastrointestinal tract. At the same time, it is easy to rinse off whatever they were fed or treated with from the exterior of their body. Our research unexpectedly showed that the administration to the nematode infected with *S. aureus* of obligatorily virulent bacteriophages specific for the infecting strain of *S. aureus* significantly reduces the mortality of the nematode at the stage when the replacement of *S. aureus* in their feed with a non-pathogenic strain of *E. coli* does not reverse the effects of the infection.

A preferable effect of the use of the method is the possibility of testing and comparing the therapeutic effectiveness of various bacteriophages in vivo, during the treatment of an infected organism. An additional preferable effect is the possibility of simple monitoring of the effects of the therapy in real time, through the evaluation of the degree of eradication of the pathogenic bacteria in the infected organism.

The present invention relates to a method of evaluating the therapeutic efficacy of bacteriophages in the treatment of bacterial infections using infected nematodes as indicator organisms as well as the use of the nematode in the evaluation of the therapeutic efficacy of bacteriophages.

The subject of the present invention is a method of evaluating the therapeutic efficacy of bacteriophages in the treatment of infections by bacterial strains characterised in that it encompasses stages in which:

a) the nematode, particularly *Caenorhabditis elegans*, is infected with an infectious bacterial strain, b) the infected nematode is put into contact with the evaluated bacteriophage, and then, c) the nematode is further cultured on a sterile medium, wherein the growth or proliferation of the infectious strain on the medium, or the lack of eradication of infectious bacteria from the nematode body as well as the depressed survival of the nematode in comparison to a group of nematodes cultured under the same conditions but not infected with infectious bacteria and not put in contact with the phage is evidence of the poor therapeutic efficacy of the evaluated bacteriophage, whereas the lack of growth or proliferation of the infectious bacterial strain, or the eradication of infectious bacterial strain from the nematode body as well as the increased survival of the nematode in comparison to those cultured under the same conditions and infected with the pathogenic bacteria, but not contacted with the bacteriophage, is indicative of a high therapeutic efficacy of the evaluated bacteriophage. Preferably:

the nematode is cultured on a medium advantageous for bacterial growth, in particular TSA, in stage b) the nematode is put into contact with phage lysate or other phage suspension, preferably with a titre of at least $1 \times 10^9$, in stage c) the culture is maintained on a medium advantageous for bacterial growth, in particular TSA.

The next subject of the present invention is a kit for evaluating the therapeutic efficacy of bacteriophages in the treatment of bacterial infections in vivo containing an indicator organism infected with an infectious bacterial strain characterised in that as the indicator organism it contains a nematode, particularly Caenorhabditis elegans.

The next subject of the present invention is the use of the nematode, particularly Caenorhabditis elegans, infected with an infectious bacterial strain for evaluating the therapeutic efficacy of bacteriophages in the treatment of infections by said bacterial strain.

Unexpectedly, it turned out that bacteriophages evaluated as lytically active against bacteria cultured in laboratory media differ in therapeutic efficacy in the treatment of the nematode.

Due to differences between the restriction-modification (R-M) systems of various strains of S. aureus of various clonal types, and the presence in these strains of mobile genetic elements encoding additional R-M systems, in the case of many strains their infection with phages amplified in a strain for proliferation is at first ineffective (only one per about $100\text{-}10^8$ cells become infected, depending on the strain). Only the phage progeny leaving this cell is modified in an appropriate fashion, and may effectively infect the cells of this strain. In such cases, during the phage infection of bacterial cells in a laboratory medium, the evident lysis of a majority of bacterial cells in the medium is observable only after a period of time. In the case of therapeutic phage applications, the effect of such a phage adaptation to a bacterial strain has not been studied, due to a lack of possibilities. A preferable characteristic of the method in question is the possibility of evaluating the therapeutic effect of phages which require adaptation to a particular strain.

Unexpectedly, it turns out that phages, which require adaptation for the infection of a given strain in vitro, are therapeutically effective for nematodes infected with this strain, but the therapeutic effect is observed with a delay. This indicated the possibility of phage adaptation in an infected organism and extends the use of the method described for evaluating adaptive capabilities of phages in vivo.

To summarize, the present invention is the first to give such broad capabilities of evaluating the therapeutic activity of bacteriophages under conditions of the pathogenic infection of a multicellular organism by bacteria. The simplicity, low costs and rapid use of the method described herein make it possible to use in large-scale studies on the therapeutic effectiveness of natural bacteriophages, but also those that have been altered through recombination or through the introduction of some mutations. The introduction of this method as a standard for the evaluation of the therapeutic efficacy of phages initially selected based on the results of in vitro studies, will make it possible to select from among them such phages, that will be both the most effective in vivo, and able to adapt for efficient proliferation in given strains in vivo without the need for a preceding adaptation in vitro.

The present invention introduces the possibility of verifying the therapeutic efficacy of the so-called temperate bacteriophages, meaning those that, depending on culture conditions, may propagate in bacteria causing bacterial cell lysis and the release of progeny phages, or which may remain in cells in a latent form (as DNA), not causing lysis. The choice of phage propagation strategy is so dependent on conditions, that without empirical studies it is impossible to predict how it will proceed in a living organism infected by bacteria that are specific hosts for such a phage. The possibility of a therapeutic use of temperate phages is a matter of discussion, as they often encode bacterial virulence factors. However, examples of therapeutic applications of temperate phages that do not encode such factors, have been described in the therapy of bacterial infections in mice. The present invention introduces the possibility of also testing temperate phages in terms of their therapeutic applicability in vivo.

An additional benefit of the present invention is the possibility of monitoring the degree of infecting bacteria eradication at each time point from the moment of administration of the phages, and by the same token of accurately evaluating the course of therapy over time, regardless of the overall conditions of infected individuals.

The description of the present invention has been supplemented with the following tables and figures.

Table 1 shows the results of an evaluation of the efficacy of the infection of strains of S. aureus with selected S. aureus bacteriophages in an in vitro assay on a solid medium.

FIG. 1 shows the results of an evaluation of the efficacy of the infection of strains of S. aureus with selected S. aureus bacteriophages in an in vitro assay in a liquid medium. Shown are the kinetics of cell lysis of selected strains of S. aureus infected with S. aureus bacteriophages in a liquid medium, at different phage:bacteria ratio (multiplicity of infection=M. O. I.). The optical density of the bacterial culture following the addition of a given phage was monitored for 24 hours using a BIOSCREEN C apparatus. The subsequent graphs show the results obtained for individual phages. Controls represent bacterial cultures that were not infected.

Figure 6:
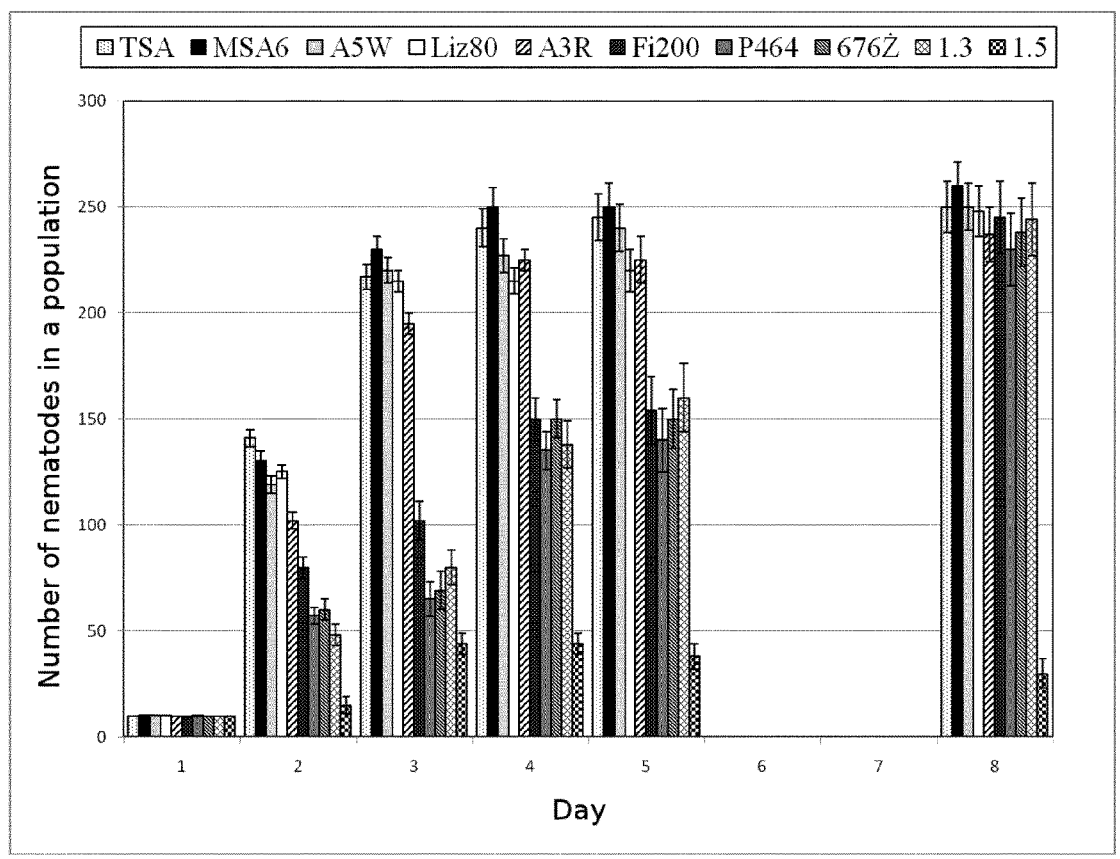

FIG. 6 shows a comparison of the nematode population fitness (as measured by the population count) on consecutive days following the end of phage therapy of *S. aureus* infections.

Figure 7:
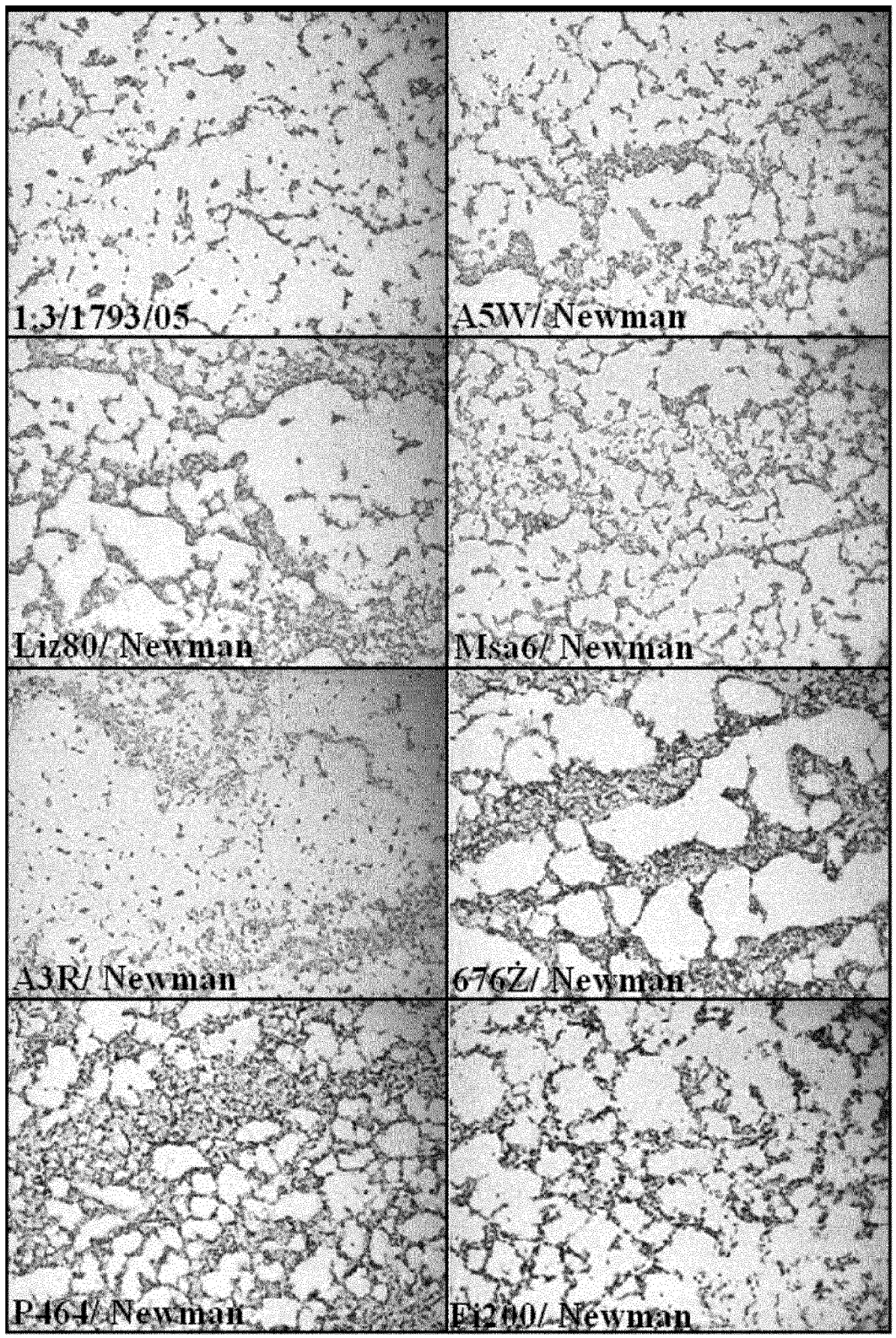

FIG. 7 shows a microscopy image of Gram-stained bacteria collected from a culture of the nematode infected with *S. aureus* and subjected to phage therapy, on the seventh day following the treatment cycle. *S. aureus*, a Gram-positive bacterium, stains gray and black. The names of the infectious strains and phages are given in the individual sections of the picture.

Figure 8:
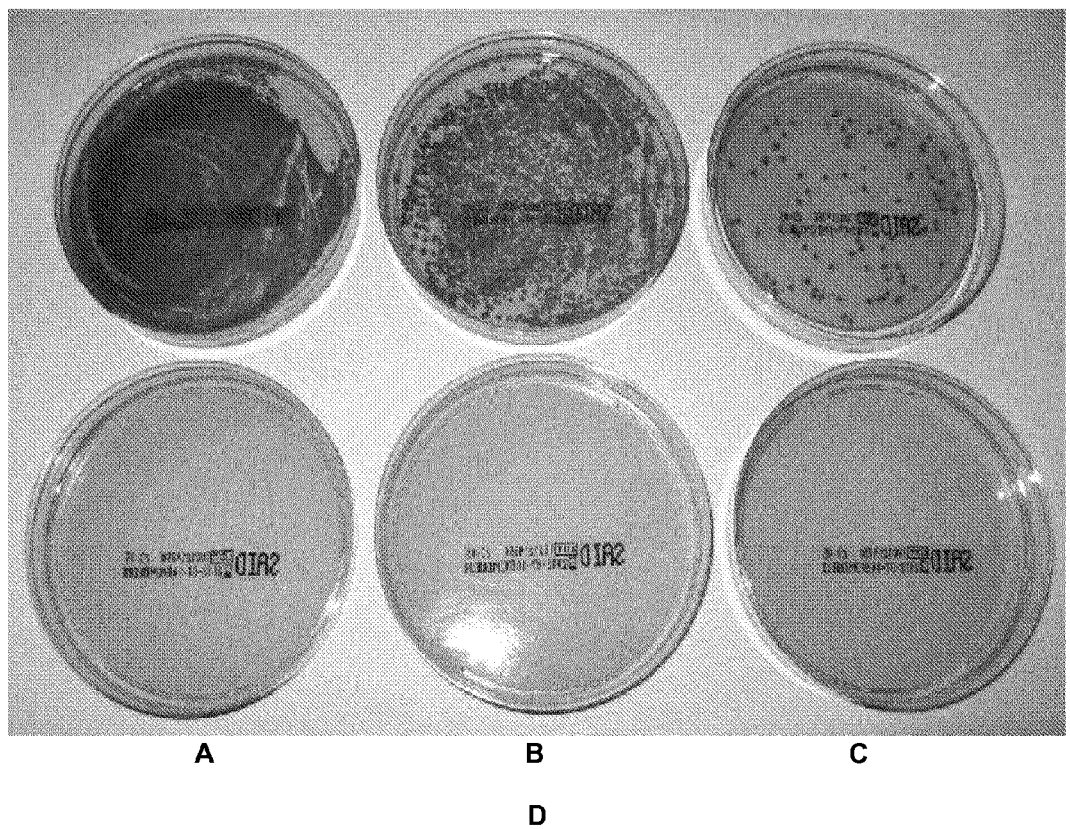
Figure 8:
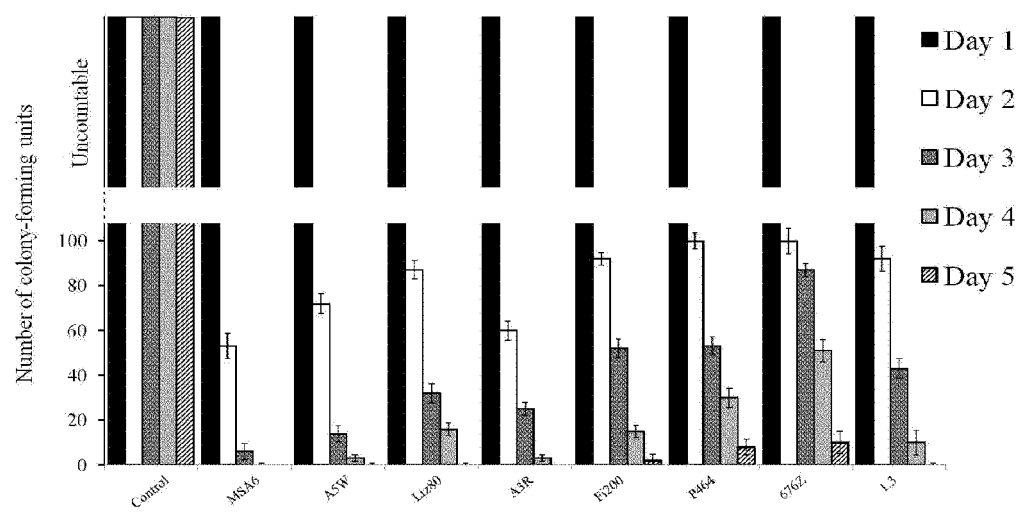

FIG. 8 shows the results of real-time monitoring of phage-mediated *S. aureus* eradication kinetics in bodies of *S. aureus* infected nematodes. Typically, dishes with a chromID *S. aureus* medium (BioMerieux), selective and differentiating for staphylococci, were incubated for 24 hours at 37° C., following spreading of concentrated or diluted suspensions of homogenates from 30 nematodes (column A—concentrated, B—$10^{-2}$, C—$10^4$), infected with cells of a given *S. aureus* strain (as exemplified by strain Pulawski in A, B, and C) and untreated (upper row) or treated with phages after five treatment cycles (bottom row). The colonies of *S. aureus* representing the progeny of bacterial cells remaining in the nematode body were differentiated on this medium from colonies of bacterial commensals inhabiting the nematode due to the blue-green staining. The average results of at least three independent counts of *S. aureus* colony forming units obtained from bodies of nematodes infected with various *S. aureus* strains, for five consecutive days following phage treatment cycle (D). For each count the medium was overlaid with a concentrated homogenate of 30 nematodes.

For a clearer understanding of the nature of the present invention, it is illustrated by the following example, which demonstrates both the therapeutic effects of bacteriophages in relation to the *S. aureus* infected nematode, as well as a comparison of the lytic efficacy of bacteriophages under laboratory conditions with their in vivo therapeutic efficacy. It also enables to evaluate the possibility of comparing the therapeutic effects of different bacteriophages on infected nematodes.

EXAMPLES

For the studies presented in the example, we selected *S. aureus* bacteriophages representing various genera as well as groups (lytic and temperate bacteriophages). The genomic sequences of all bacteriophages used have been determined. The bacteriophages were obtained from the following sources:

A5W, A3R, P464 (=P4W), Fi200 (=Fi200W), 676Z, Liz80 (=Staph1N)—the collection of the Ludwik Hirszfeld Institute of Immunology and Experimental Therapy PAN (IIET)

MSA6—a bacteriophage from the Military Institute of Hygiene and Epidemiology (MIHE), evaluated at the auspices of the targeted project PBZ-MNiSW-04/I/2007 in collaboration with this institute, as well as with the Autonomous Department of Microorganisms' Biology at the Faculty of Agriculture and Biology of the Warsaw University of Life Sciences (ADMB)

phiAGO1.3, phiAGO1.5—bacteriophages isolated at the Department of Microbial Biochemistry of the IBB PAN (DMB), in collaboration with the National Medicines Institute (NMI) as part of the targeted project PBZ-MNiSW-04/I/2007; evaluated under the auspices of the targeted project in collaboration with NMI and ADMB.

The following were selected as example strains of *S. aureus* that cause infection:

*S. aureus* Newman—standard strain used for evaluating the pathogenicity of *S. aureus* due to the stability of its agr locus, which is a regulator of certain virulence determinants; obtained in collaboration with NMI, the molecular characteristics of the strain are given in literature sources the clinical strains of *S. aureus*: 1793/05, 300/07, 4065/07 as well as 18.6—obtained and molecularly characterized in collaboration with NMI strain *S. aureus* Pulawski (25923™, ATCC collection) from MIHE, studied in collaboration with MIHE and ADMB as part of the targeted project PBZ-MNiSW-04/I/2007 strain *S. aureus* 80/DPN (=PS80bf2)—a derivative of the epidemiological *S. aureus* PS80 strain obtained from Prof. Galiński (Department of Medical Microbiology, Medical University of Gdansk), modified as part of the POIG.01.03.01-00-003/08 project and characterised in collaboration with the NMI the strains R19930/DPN, Z11788/DPN and 6409/DPN—strains for phage propagation obtained from the collection of the IIET and modified as part of the POIG.01.03.01-00-003/08 project.

In order to obtain data for comparative analyses, we evaluated the lytic efficacy of the tested bacteriophages under laboratory conditions. The evaluation was performed using two methods: via a spot test on solid media, as well as by assaying bacterial lysis in liquid media.

Evaluation of the Bacteriophage Lytic Efficacy by Using a Spot Test 0.1 ml of an overnight culture of a selected strain of *S. aureus* conducted on LB medium were supplemented with 0.1 ml 0.025 M of a solution of $CaCl_2$ and $MgSO_4$. Next, the mixture was supplemented with 1 ml of LB medium as well as 4 ml of LCA medium dissolved and cooled to 55° C. and cast onto the surface of dishes with LB medium. The reverse side of the dishes was marked with 6 sectors. Phage lysates were prepared such that the multiplicity of infection (M.O.I.) was respectively: 1; 0.5; 0.1; 0.05; 0.01. The lysates were obtained from strains selected for amplifying individual phages. Plates with a formed bacterial layer were spotted with 15 μl of the appropriate lysate per sector. The plates were incubated overnight at a temperature of 37° C. as well as 25° C.

For each of phages we prepared a plate with a layer of an appropriate *S. aureus* indicator strain as a control.

After the indicated incubation period, we observed whether clear zones or plaques formed in the bacterial layer at the sites of lysate drops. We also described the appearance of the clear zones or plaques.

Each of the evaluated bacteriophages amplified in cells of its propagation strain infected the tested strain, but the infection efficiency varied (Table 1). Phages P464, 676Ż as well as phiAGO1.5 infected cells of the tested strains with a much lower efficiency than the cells of their propagation strains. Furthermore, some phages which formed clear plaques on cell layers of their propagation strain formed turbid plaques on cell layers of tested strain.

Evaluation of the Lytic Efficacy of Bacteriophages in a Liquid Medium

Overnight cultures of *S. aureus* strains were diluted 1:100 with fresh LB medium supplemented with $CaCl_2$ and MgSO$_4$ to a final concentration of 0.01 M. Next, multi-well plate wells were loaded with 190 μl of the culture and incubated in a Bioscreen apparatus at a temperature of 25° C. until reaching an optical density of OD$_{600}$~0.1. Phage lysates were prepared such that the M.O.I was: 1; 0.5; 0.1; 0.05 and 0.01. The lysates were obtained from strains for the propagation of the individual phages. After the incubation, the wells were supplemented with 10 μl each of an appropriate phage lysate. The mixtures of bacteria with phages were left for 10 minutes at room temperature to facilitate adsorption of phages from the lysate onto the surface of bacterial cells. Next, the plates were placed in a Bioscreen apparatus, set for the following conditions: incubation temperature 25° C., wavelength for culture OD measurement: 600 nm, rotation speed "medium", interval between measurements: 15 minutes, experiment duration: 24 hours. The experiment was performed against controls—uninfected cultures of all bacterial strains used in the experiment as well as LB medium with an addition of CaCl$_2$ and MgSO$_4$, to a final concentration of 0.01 M.

Figure 1:
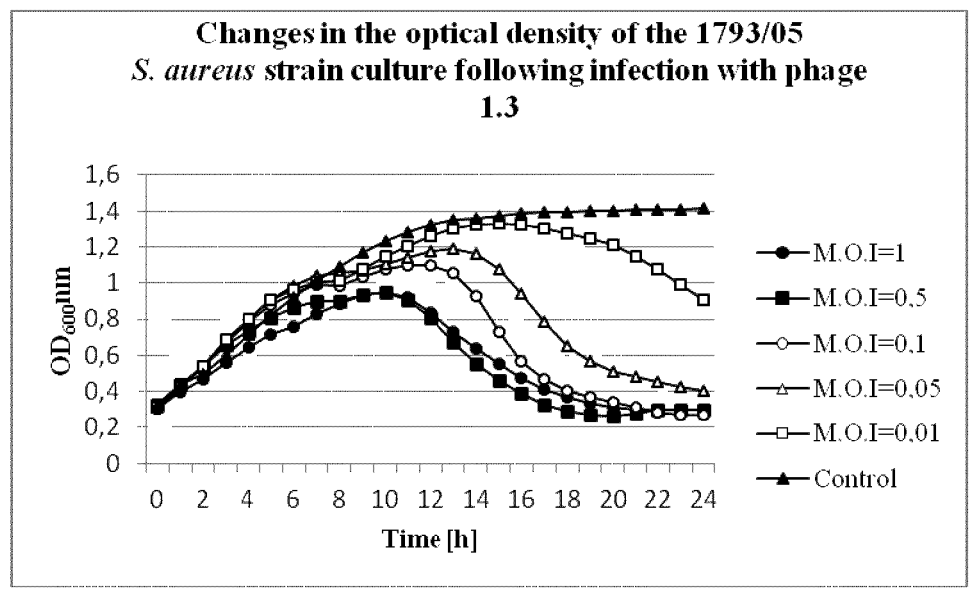
Figure 1:
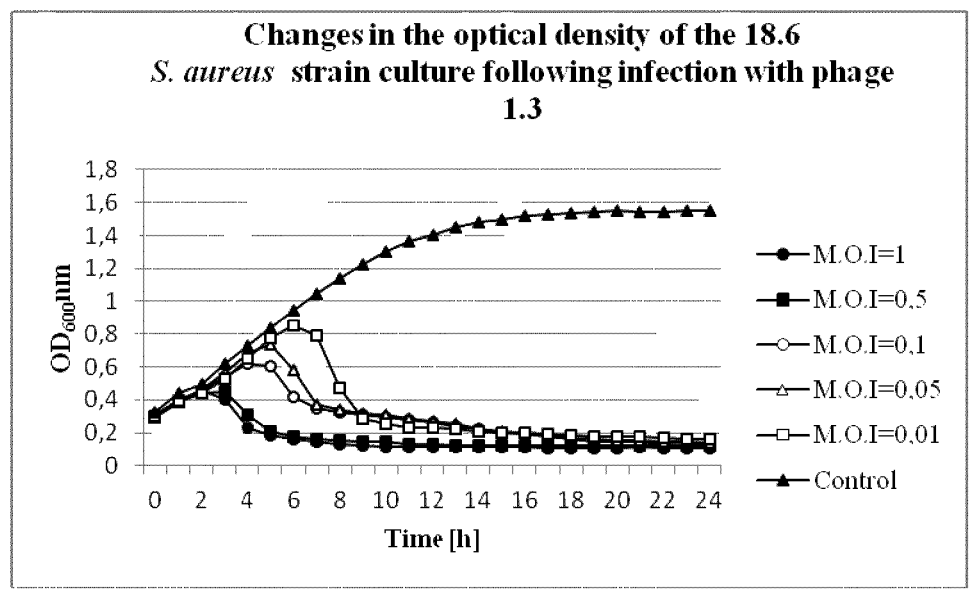
Figure 1:
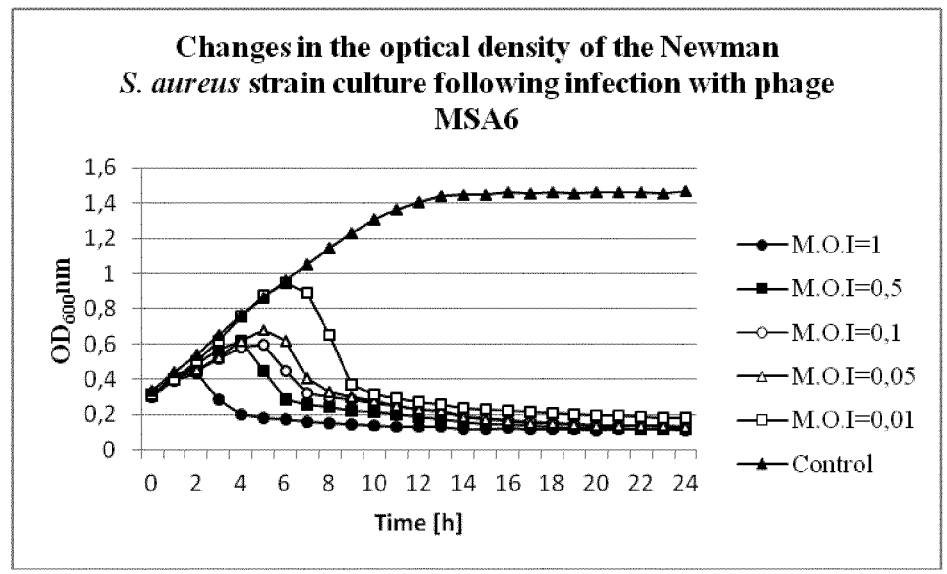
Figure 1:
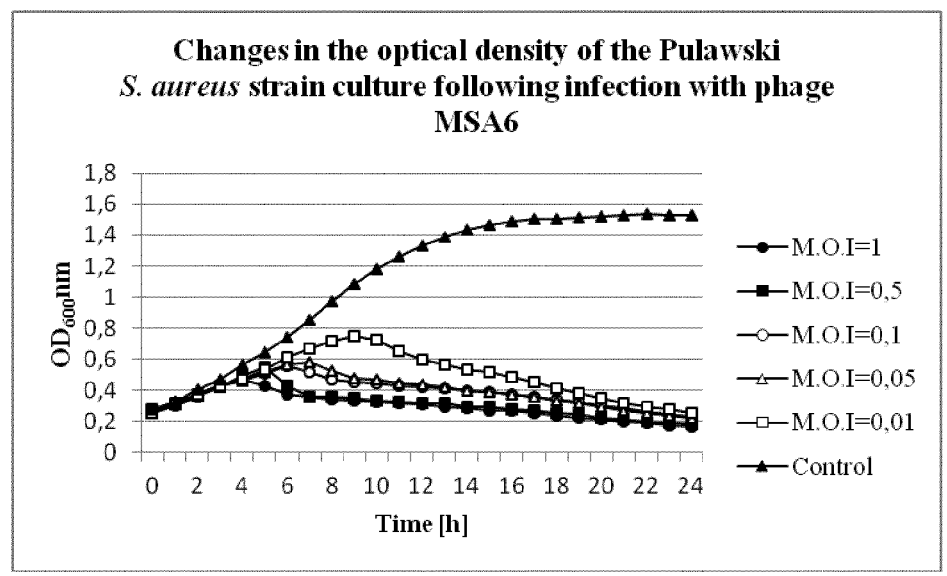
Figure 1:
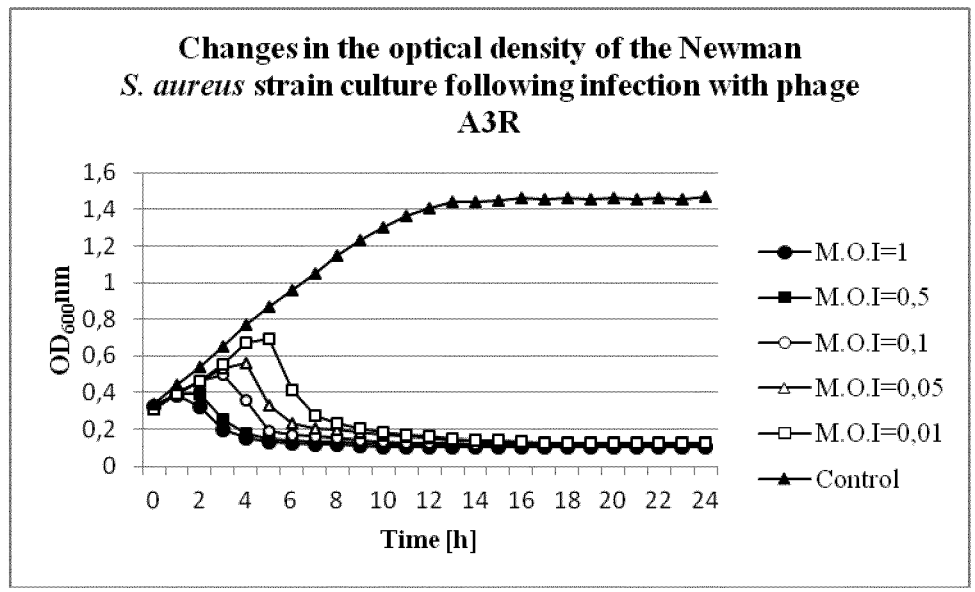
Figure 1:
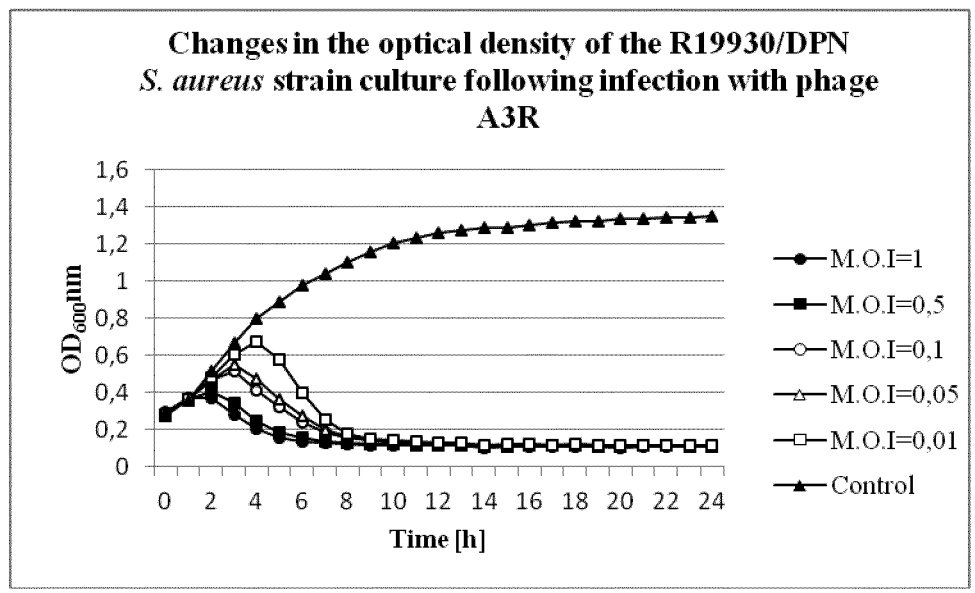
Figure 1:
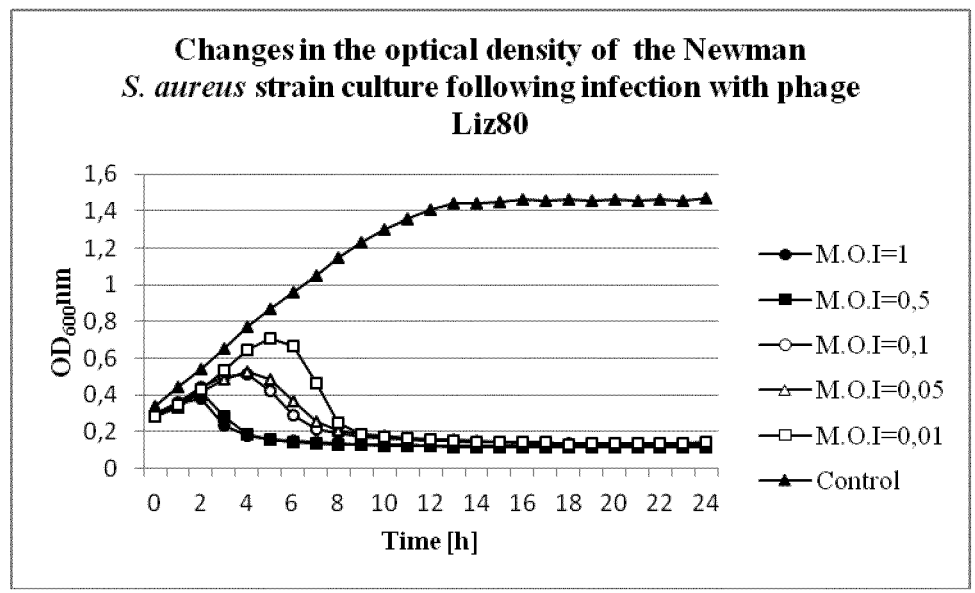
Figure 1:
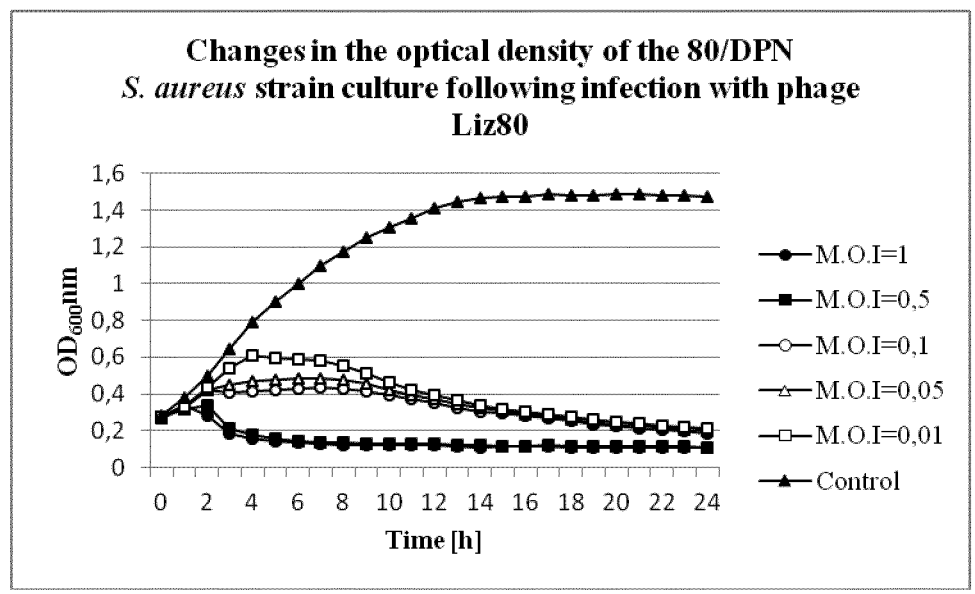
Figure 1:
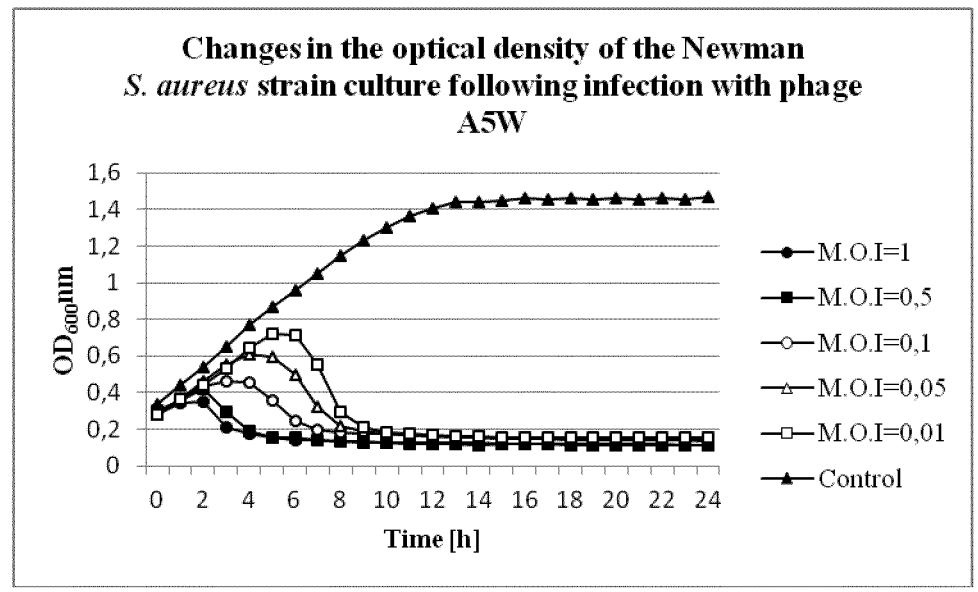
Figure 1:
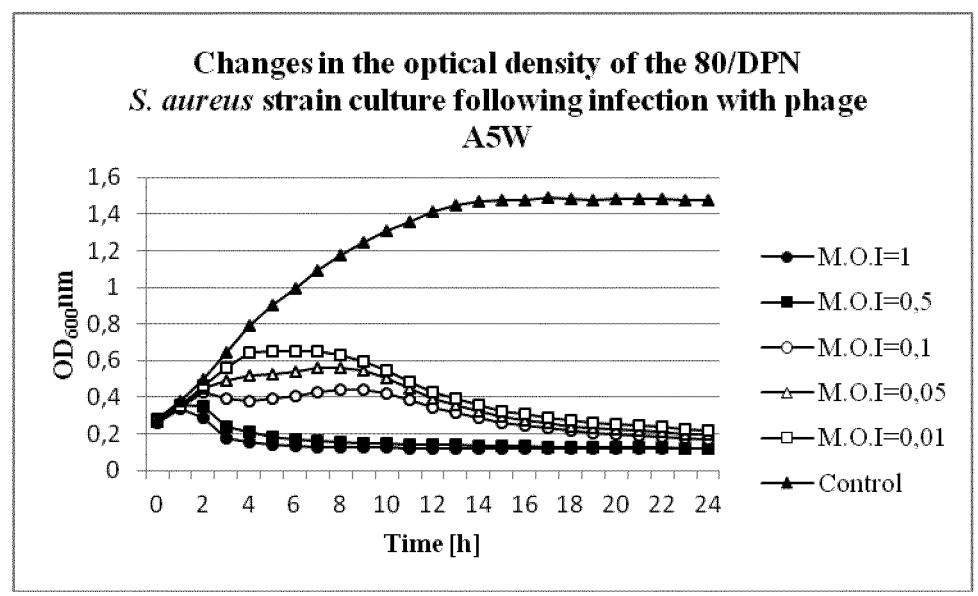
Figure 1:
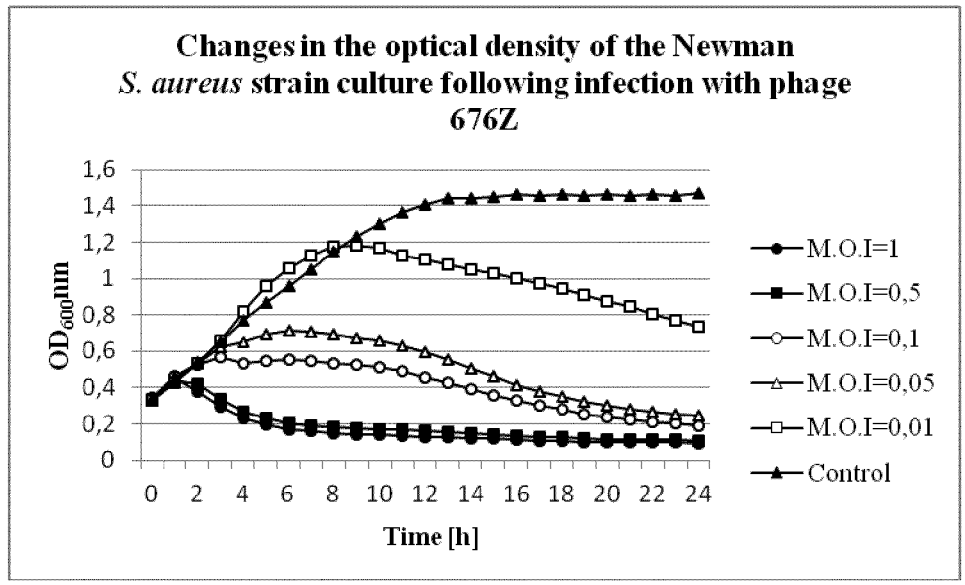
Figure 1:
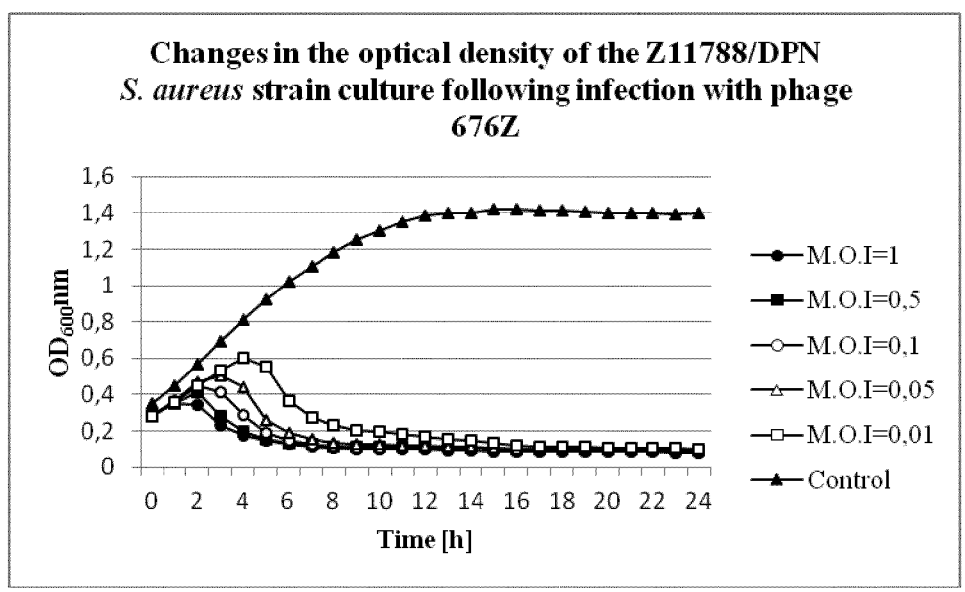
Figure 1:
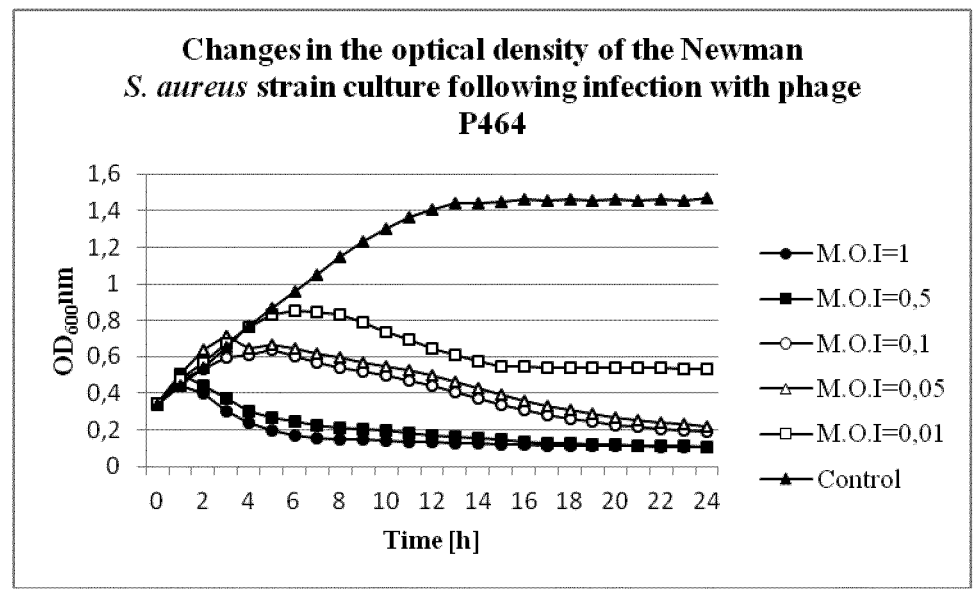
Figure 1:
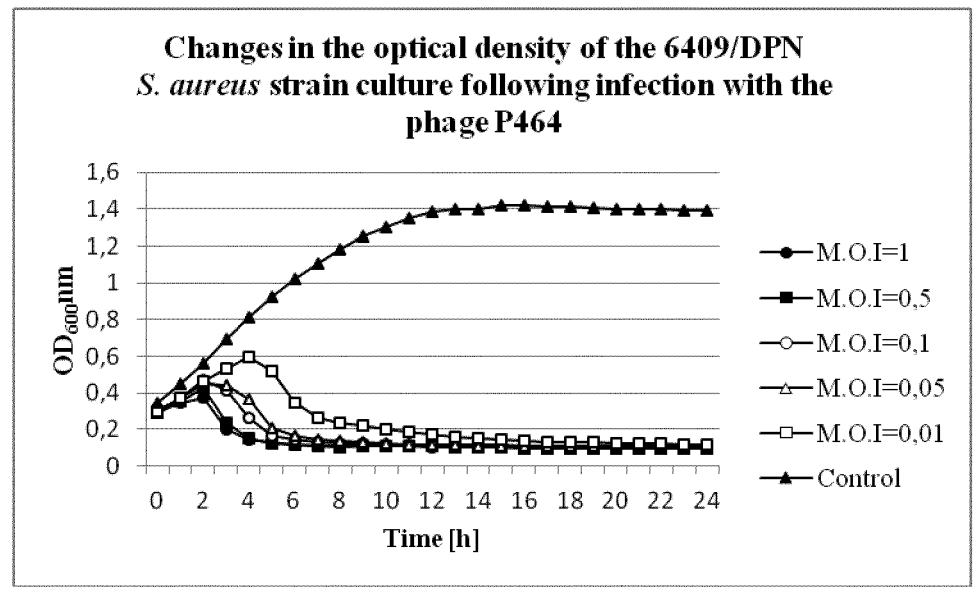
Figure 1:
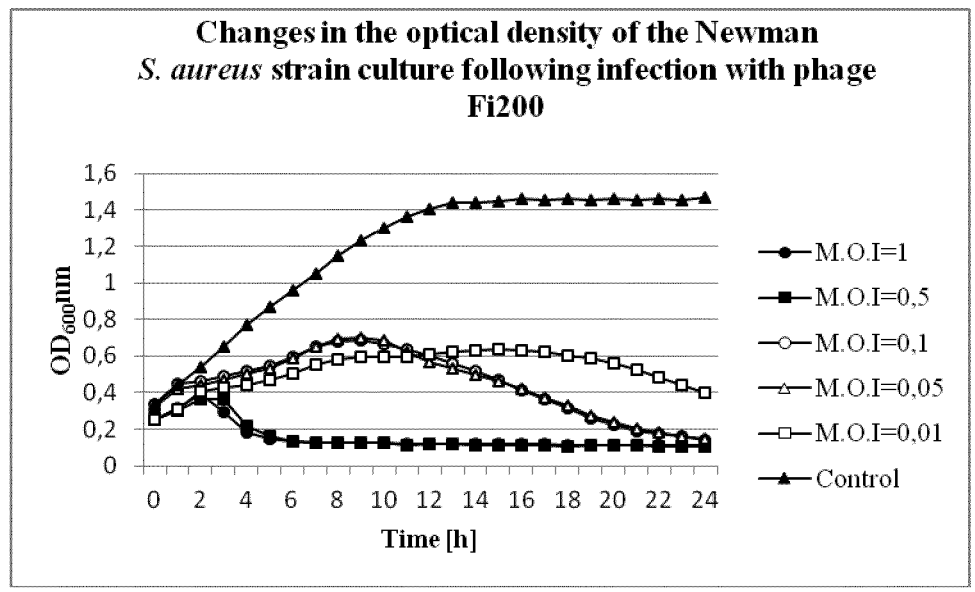
Figure 1:
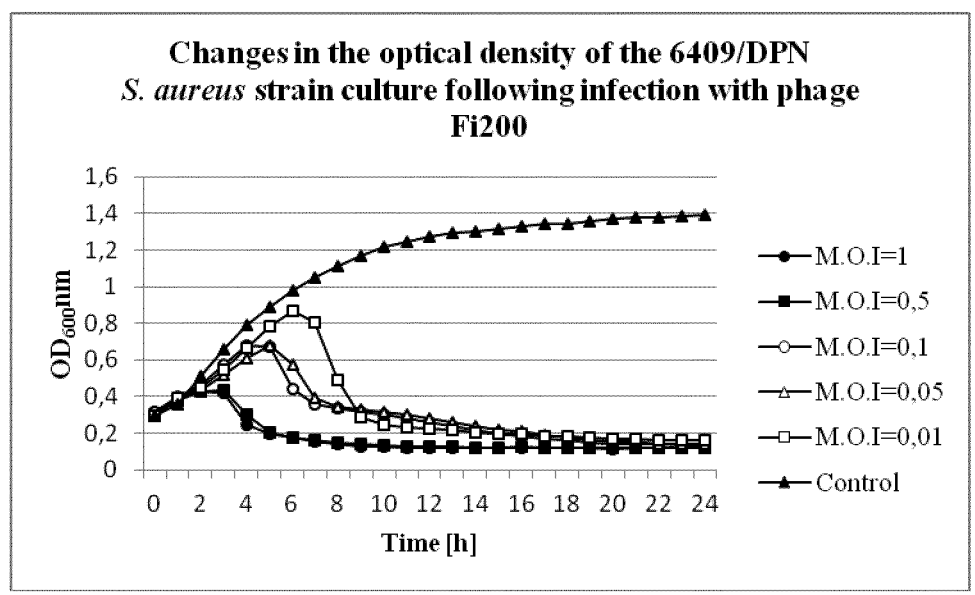
Figure 1:
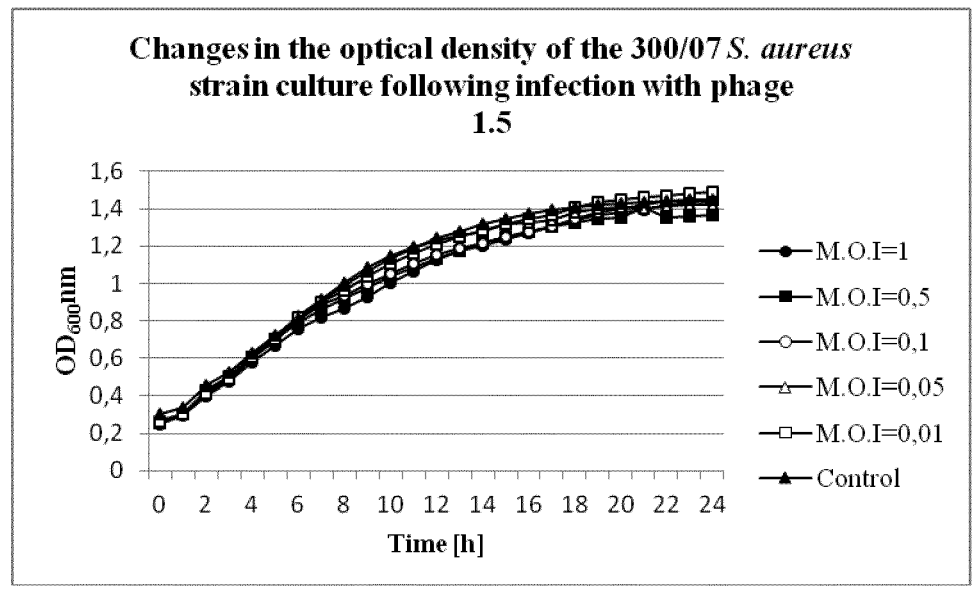
Figure 1:
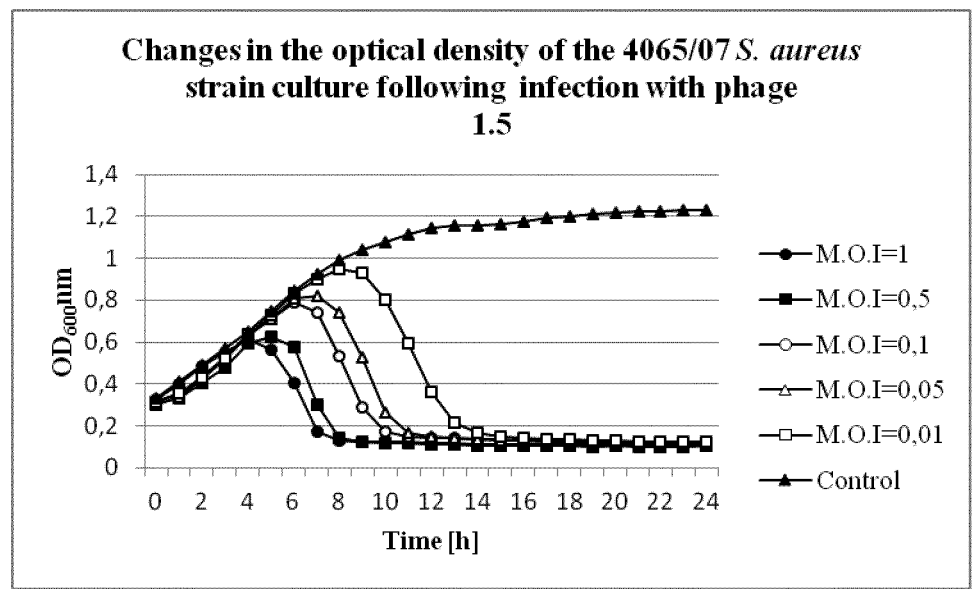

The kinetics of cell lysis in the cultures of various strains infected with the individual phages showed similarities which were unequivocally indicative of a high infectious and lytic efficacy of the phages only at high multiplicities of infection (M.O.I.; FIG. 1). At lower multiplicities of infection we observed clear differences in infected cell lysis kinetics in cultures of bacteria infected with individual phages. In the case of phage phiAGO1.5, even at M.O.I. of 1, we observed lysis only after 5 or 6 hours from the moment of infection. Moreover, some phages exhibited a decidedly smaller or delayed lytic activity in relation to testing strains than against their propagation strains.

In order to ascertain whether and how these differences correlate with the therapeutic activity of bacteriophages in vivo, we performed tests using the nematode as a model host for infectious strains of *S. aureus*. These tests were performed using the following experimental schemes according to original methods that were developed for the purposes of the present invention.

Method of Evaluating the Efficacy of Phage Therapy In Vivo in a Model System of the Nematode *C. elegans* Infected with Pathogenic *S. aureus* Strains Initial Evaluation of the Therapeutic Efficacy of Bacteriophages with the Approximate Method A rapid evaluation of the efficacy of bacteriophages in limiting the staphylococcal gut infection of *C. elegans* was performed using a multi-stage experiment. First, the nematodes were given a selected strain of *S. aureus* as a sole source of nutrients. After 24 hours, infected individuals were rinsed and incubated for 1 hour in a phage lysate or LB medium (control). LB medium composition: 0.5% (mass/vol.) yeast extract, 1% (mass/vol.) bacto tryptone, 0.5% (mass/vol.) NaCl in double-distilled water. Next, the nematodes were transferred onto Petri dishes with TSA medium (composition per litre of distilled water:pancreatic casein peptone: 15.0 g, papainic soya peptone: 5.0 g, NaCl: 5.0 g, bacto agar: 15 g).

Figure 2:
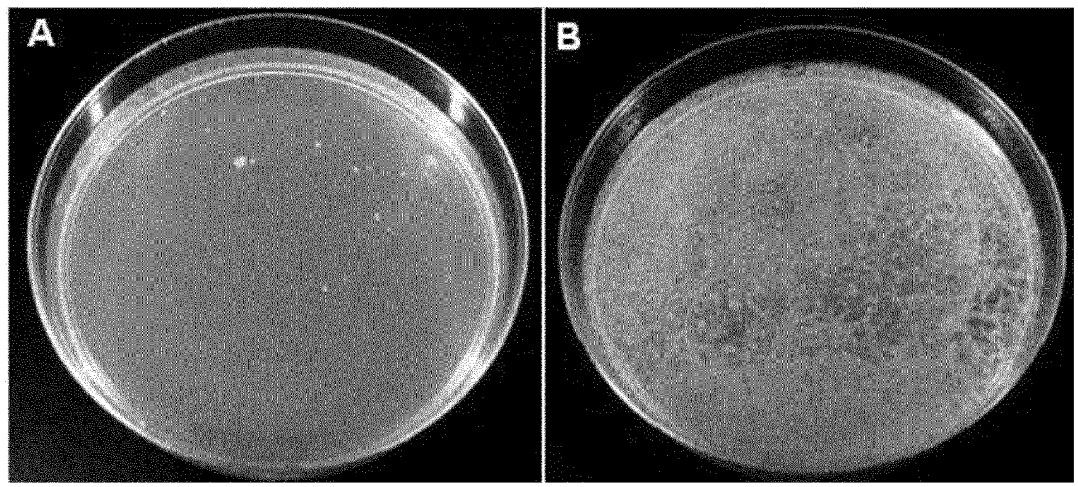
FIG. 2 shows the appearance of a culture of the nematode C. elegans infected with the strain S. aureus Newman in the 24-th hour following rinsing in a lysate of bacteriophage MSA6 (A) or LB medium (control) (B).

A large difference was observed between the plates containing transferred nematodes following the incubation with lysate in comparison to the control plates. Plates containing the nematodes treated with phages contained only the nematodes, whereas control plates were densely populated with bacteria (FIG. 2). This indicates the presence of numerous, viable and colony-forming bacteria in the control nematode feces, and the lack thereof in the feces of the nematodes treated with phages.

Evaluation of the Therapeutic Efficacy of Bacteriophages—Precise Method

1. Infection of Nematodes:

Twenty to thirty 2-3 day old nematodes (*C. elegans*) were placed on Petri dishes with TSA medium. Next, the medium was overlaid with 0.6 ml of an overnight *S. aureus* culture grown in TSB medium (composition per litre of distilled water:pancreatic casein hydrolysate: 17.0 g, soybean meal papain hydrolysate: 3.0 g, NaCl: 5.0 g, potassium biphosphate: 2.5 g, dextrose: 2.5 g), then this was spread around evenly and left to absorb. The dishes were incubated at 25° C. for 24 hours.

2. Administration of Bacteriophages

After 24 hours of incubation, the nematodes were placed on nylon meshes (CellMicroSieves, BioDesign) with a pore diameter of 10 μm and were rinsed twice with 5 ml of LB medium, and then transferred onto TSA medium. The cultures were covered with 5 ml of phage lysate with a titre of 1×10$^9$, and incubated at room temperature for 2 hours. In parallel, a control procedure was performed, wherein the nematodes were covered with 5 ml of LB medium. After the incubation, the nematodes were placed onto nylon meshes, rinsed twice with 5 ml of LB medium, and then transferred onto TSA medium. The dishes were incubated at a temperature of 25° C.

In order to evaluate the possibility of a complete cure of the nematode infected with *S. aureus* using phage therapy, the treatment was performed 5 times at 24-hour intervals.

Figure 3:
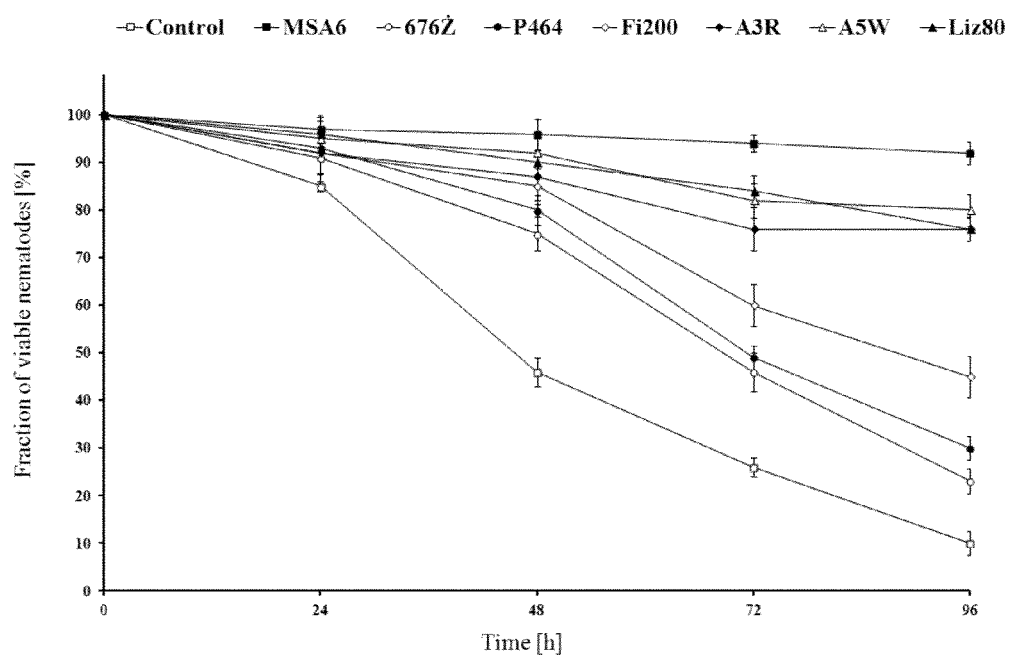
FIG. 3 shows the results of a comparison of the survival of the nematodes infected with the S. aureus Newman strain subjected to a cycle of treatment with bacteriophages A3R, A5W, Liz80, Fi200, P464, 676Ż, MSA6 as well as untreated ones. All of the evaluated bacteriophages are of the Twort-like type.
Figure 4:
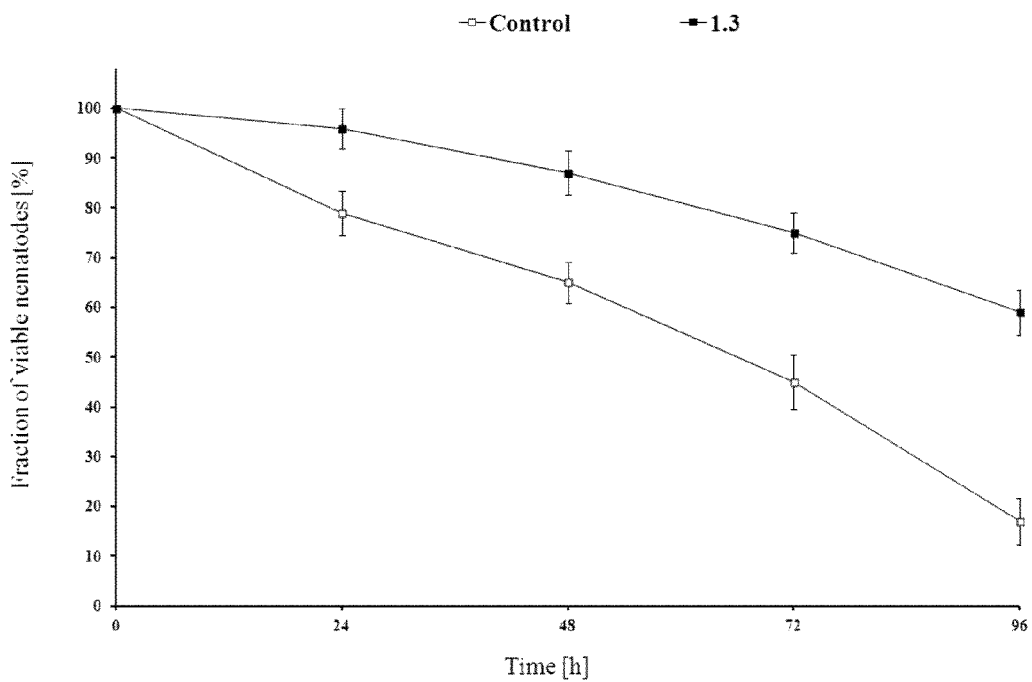
FIG. 4 shows the results of a comparison of the survival of the nematodes infected with the clinical strain S. aureus 1793/05 and untreated ones as well as those treated with obligatorily lytic, polyvalent bacteriophage phiAGO1.3 of the AHJD-like species.
Figure 5:
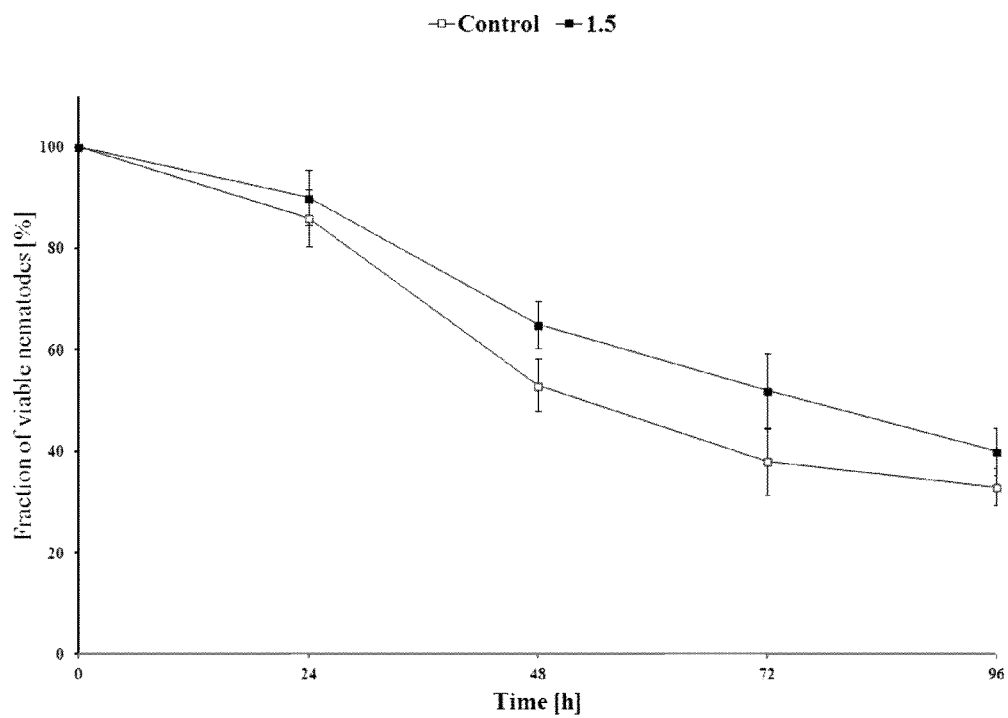
FIG. 5 shows the results of a comparison of the survival of the nematodes infected with the clinical S. aureus 300/07 strain and untreated ones as well as those treated with the temperate, polyvalent bacteriophage phiAGO1.5 of the Siphoviridae family.

3. Evaluation of the Therapeutic Efficacy a) Following each dose of therapeutic phages, 30 nematodes were rinsed four times with 5 ml LB medium and crushed in a buffer to prepare body homogenates that served to assay the number of viable *S. aureus* cells in a nematode body, by counting the number *S. aureus* colony forming units on a selective and differentiating medium (FIG. 8).

b) Following the last dose of therapeutic phages, the nematodes were put under a 5-day observation, during which the deceased individuals were counted (FIGS. 3, 4 and 5).

c) After 7 days following the completion of the therapy, we transferred the nematodes onto TSA medium in batches of 10-30. The dishes were incubated at a temperature of 25° C. The observations were conducted over 5 days, every 24 hours. We observed such parameters as motility, appearance and population counts (FIG. 6).

d) After 7 days following the end of therapy, we made microscope slides from bacteria growing in the nematode cultures, and stained them using the Gram protocol (FIG. 7).

The use of the above assays of phage activity evaluation on infected nematodes enabled us to select phage MSA6 as the most therapeutically effective phage from amongst the Twort-like phages that were generally very similar in in vitro assays. As a result of the therapeutic use of this phage, the survival of the infected nematodes increased from 12% to almost 90% (FIG. 3). The low mortality also characterised the nematodes that were given lysates of phages A3R, A5W or Liz80. The survival of these nematodes increased to 76%, 80% or 76% respectively. On microscope slides of bacteria extracted from the culture of the nematode subjected to treatment with the abovementioned phages, we observed only Gram-negative bacteria (FIG. 7), and the nematodes transferred onto fresh TSA medium quickly regained a fitness comparable to the fitness of uninfected individuals that were maintained under the same conditions (FIG. 6).

Therapy with the phage Fi200 was less effective, with about 50% of the treated population dying (FIG. 3). A relatively high mortality characterised nematodes treated with P464 as well as 676Ż. At the same time, nematodes treated with phages Fi200, 676Ż or P464 transferred onto fresh TSA medium exhibited a depressed population growth dynamic—their populations reached abundance comparable to the abundance of uninfected nematode population only by the eighth day of incubation (FIG. 6). In all of the nematode cultures treated with the indicated three phages, we observed Gram-negative and Gram-positive bacteria (FIG. 7).

The completely unexpected observation was that, even in the case of treatment with the less therapeutically effective phages (P464, 676Ż and Fi200), individuals which survived due to the therapy and were isolated from the population, also returned to full health and reproductive ability, but after a longer period than individuals treated with the more therapeutically effective phages (MSA6, A5W, Liz80 and A3R) (FIG. 6).

The survival of the nematodes infected with strain 1793/05 of S. aureus and subjected to treatment with the newly-isolated, obligatorily virulent and polyvalent bacteriophage phiAGO1.3, representing the AHJD-like type, was significantly higher in comparison to individuals infected but not treated and was about 65% (FIG. 5). In nematode cultures treated with this phage, we observed solely Gram-negative bacteria (FIG. 7). Although nematodes treated with this phage and transferred onto fresh TSA medium exhibited a slightly depressed population growth dynamic, after 8 days this population attained abundance comparable to the abundance of uninfected nematode population (FIG. 6). Three phages have been described so far, which are highly homologous in terms of genomic sequence to the phage phiAGO1.3. Although their obligatorily lytic nature and polyvalence have allowed the authors to speculate about their therapeutic utility, no one to date has shown that they could be therapeutically effective. This has become possible due to the method described herein.

A different result was obtained in the case of treatment of infected nematodes with temperate phage phiAGO1.5. The mortality of nematodes infected with the 300/07 strain of S. aureus subjected to a cycle of treatment with bacteriophage phiAGO1.5 was similar to that of the nematodes infected but not treated (FIG. 4). Gram positive bacteria were observed in the cultures (FIG. 7), and the nematodes transferred onto fresh TSA medium continued to die off (FIG. 6). Although this suggests the elimination of this phage from among potentially therapeutic phages, it will be possible to test its subsequent mutants that are incapable of lysogeny in the nematode model system.

Evaluation of the Degree of Eradication of the Pathogenic Bacteria Inside the Organism of the Nematode in Real Time During Therapy For the accurate evaluation of the therapeutic efficacy of the bacteriophages, the treatments of the nematodes infected with S. aureus with phages, were performed 5 times at 24 hour intervals, as described above. After the last dose of therapeutic phages, the cultures were incubated for 48 hours at a temperature of 25° C. After the end of the incubation, the nematodes were placed on nylon meshes and were rinsed four times in 5 ml of LB medium. Next, about 30 of the nematodes were suspended in 300 μl of buffer M9 and ground. From the resulting homogenate we obtained the following dilutions: $10^0$, $10^{-2}$, $10^{-4}$, $10^{-6}$. Indicator dishes with chromID S. aureus medium (bioMerieux, only staphylococci grow on these) we inoculated 100 μl aliquots of undiluted homogenate, or its various dilutions and incubated them at a temperature of 37° C., for 24 hours. Similar assays were performed after each single cycle of treatment with the phages in the course of 5-day therapy. The numbers of living S. aureus cells left in the nematodes after each cycle of treatment were determined based on the number of S. aureus colonies on indicator dishes.

SUMMARY

In the present invention, C. elegans was used for the first time as a model organism in the evaluation of the efficacy of phage therapy as a method of fighting bacterial infections. As an example demonstrating the efficacy of this method, we selected the infection by pathogenic strains of Staphylococcus aureus. We assayed the therapeutic efficacy of phages representing all known families of polyvalent phages that infect Staphylococcus strains. We designed an experimental schematic which enables a rapid evaluation of the therapeutic efficacy of phages in an in vivo system. The treatment was based on rinsing infected nematodes in a lysate of a given phage, conducted 5 times at 24-hour intervals. The effectiveness of the therapy was evaluated on the basis of (i) the microscopy images of Gram-stained bacteria collected from a culture of the nematode on the seventh day following the termination of the treatment, (ii) survival profiles of the treated nematodes in comparison to untreated ones, (iii) the rate of restitution of full reproductive potential by the treated nematodes, (iv) the degree of eradication of the pathogenic bacteria from the nematode bodies after each single phage treatment during the 5-day therapy. In parallel, we tested the specificity of staphylococcal bacteriophages against several strains of S. aureus as well as their lytic efficacy in vitro—in a liquid medium and on a solid medium. This made it possible to obtain a full picture of the entire course of the infection process, which was an important control of in vivo experiments. Based on a comparison of the results obtained in both systems, it was observed that the efficacy of the infection may differ between in vivo and in vitro conditions. The use of the abovementioned method should thus be a standard during the initial testing of the therapeutic potential of bacteriophages meant for the treatment of infections in animals and humans.

The present strategy makes it possible to select, from among a pool of tested bacteriophages, the most specific ones against a given strain in vivo, by the same token ensuring the highest efficacy of treatment. The initial verification and elimination of poorly effective phages at the stage of testing on the nematodes can significantly limit the number of experiments in mammals, and significantly advance the possibility of approval for phage therapy for widespread use in the treatment of bacterial infections. The method designed furthermore facilitates scaling up, both making it possible to use it to screen extant large collections of therapeutic phages, as well as novel phages and phages obtained via recombination or mutagenesis in vitro and in vivo.

Current research on the above method includes:

1.1) Its adaptation to the evaluation of therapeutic phage efficacy in vivo at a temperature of 37° C.

1.2) Continuation of the testing of the degree of eradication of the population of S. aureus in infected nematodes at consecutive time points from the initiation of the therapy.

1.3) Continuation of the testing of "adaptation" of the bacteriophages to otherwise poorly infected strains of bacteria in vivo.

TABLE 1 A comparison of the infectiousness of *S. aureus* bacteriophages against selected strains of *S. aureus* in assays on a solid medium.

TABLE 1

A comparison of the infectiousness of *S. aureus* bacteriophages against selected strains of *S. aureus* in assays on a solid medium.

| Phage | Time [h] | Temperature | Strain of *S. aureus* | Infection coefficient | | | |
|---|---|---|---|---|---|---|---|
| | | | | 1 | 0.5 | 0.1 | 0.05 |
| A3R | 24 | 37 | Parental | CL | CL | CL | CL |
| | | | Tested | CL | CL | CL | CL |
| | 24 | 25 | Parental | CL | CL | CL | CL |
| | | | Tested | CL | CL | CL | CL |
| | 48 | 25 | Parental | CL | CL | CL | CL |
| | | | Tested | CL | CL | CL | CL |
| A5W | 24 | 37 | Parental | CL | CL | CL | CL |
| | | | Tested | CL | CL | CL | CL |
| | 24 | 25 | Parental | CL | CL | SCL | SCL |
| | | | Tested | CL | CL | SCL | SCL |
| | 48 | 25 | Parental | CL | CL | CL | CL |
| | | | Tested | CL | CL | CL | CL |
| Liz80 | 24 | 37 | Parental | CL | CL | CL | CL |
| | | | Tested | CL | CL | CL | CL |
| | 24 | 25 | Parental | SCL | SCL | SCL | SCL |
| | | | Tested | SCL | SCL | SCL | SCL |
| | 48 | 25 | Parental | CL | CL | CL | CL |
| | | | Tested | CL | CL | CL | CL |
| MSA6 | 24 | 37 | Parental | CL | CL | CL | CL |
| | | | Tested | CL | CL | CL | CL |
| | 24 | 25 | Parental | SCL | SCL | SCL | SCL |
| | | | Tested | SCL | SCL | SCL | SCL |
| | 48 | 25 | Parental | CL | CL | SCL | SCL |
| | | | Tested | CL | CL | CL | CL |
| Fi200 | 24 | 37 | Parental | CL | CL | CL | CL |
| | | | Tested | SCL | SCL | SCL | SCL |
| | 24 | 25 | Parental | CL | CL | CL | SCL |
| | | | Tested | SCL | SCL | SCL | SCL |
| | 48 | 25 | Parental | CL | CL | CL | CL |
| | | | Tested | CL | CL | SCL | SCL |
| P464 | 24 | 37 | Parental | CL | CL | CL | CL |
| | | | Tested | SCL | SCL | SCL | .. |
| | 24 | 25 | Parental | CL | CL | SCL | SCL |
| | | | Tested | SCL | SCL | SCL | SCL |
| | 48 | 25 | Parental | CL | CL | CL | SCL |
| | | | Tested | CL | CL | SCL | SCL |
| 676Z | 24 | 37 | Parental | CL | CL | CL | SCL |
| | | | Tested | SCL | SCL | SCL | .. |
| | 24 | 25 | Parental | SCL | SCL | SCL | SCL |
| | | | Tested | SCL | SCL | SCL | VSCL |
| | 48 | 25 | Parental | CL | CL | SCL | SCL |
| | | | Tested | CL | CL | SCL | SCL |
| 1.3 | 24 | 37 | Parental | CL | CL | CL | CL |
| | | | Tested | SCL | SCL | SCL | SCL |
| | 24 | 25 | Parental | CL | CL | CL | CL |
| | | | Tested | SCL | SCL | SCL | VSCL |
| | 48 | 25 | Parental | CL | CL | CL | CL |
| | | | Tested | SCL | SCL | SCL | SCL |
| 1.5 | 24 | 37 | Parental | CL | CL | CL | CL |
| | | | Tested | ++ | + | + | .. |
| | 24 | 25 | Parental | CL | CL | CL | CL |
| | | | Tested | SCL | SCL | SCL | .. |
| | 48 | 25 | Parental | CL | CL | CL | CL |
| | | | Tested | SCL | SCL | + | + |

Table markings according to Rippon J. E. 1956. The classification of bacteriophages lysing *staphylococci*. J Hyg (Lond). 54(2), 213-226. Modified.
Where:
CL = lysis,
SCL = turbid lysis,
VSL = very turbid lysis,
++ = over 50 plaques,
+ = 20-50 plaques,
+− = less than 20 plaques,
.. = no lysis

The invention claimed is:

1. A method of treating bacterial infection in a mammal in need thereof comprising (a) infecting a plurality of nematodes, in a medium with an infectious bacterial strain causing the infection in said mammal, (b) rinsing the nematodes with a medium that is free of the infectious bacterial strain, (c) incubating the rinsed nematodes in a medium comprising a phage lysate, (d) assessing nematodes response profile to identify the bacteriophage therapy candidate, wherein the lack of growth of the infectious bacterial strain, or the eradication of infectious bacterial strain from the nematode body as well as the increased survival of these nematodes in comparison to the nematodes cultured under identical conditions but infected with infectious bacteria and not put into contact with the bacteriophages is evidence of the bacteriophage therapy candidate, and (e) administering the identified bacteriophage therapy candidate to said mammal.

2. The method of claim 1, wherein the nematode is *Caenorhabditis elegans*.

3. The method of claim 1, wherein the infectious bacterial strain belongs to the genera selected from the group consisting of *Staphylococcus, Enterococcus, Pseudomonas, Salmonella, Shigella, Vibrio, Escherichia, Cronobacter* and combinations thereof.

4. The method of claim 3, wherein the infectious bacterial strain is *Staphylococcus aureus*.

* * * * *